United States Patent
Tabacco et al.

(10) Patent No.: US 6,485,962 B1
(45) Date of Patent: Nov. 26, 2002

(54) METHODS FOR SIGNAL ENHANCEMENT IN OPTICAL MICROORGANISM SENSORS

(75) Inventors: Mary Beth Tabacco, Boston; Han Chuang, Canton; John Anthony Schanzle, Belmont, all of MA (US)

(73) Assignee: Echo Technologies, Alexandria, VA (US)

( * ) Notice: Subject to any disclaimer, the term of this patent is extended or adjusted under 35 U.S.C. 154(b) by 68 days.

(21) Appl. No.: 09/628,031

(22) Filed: Jul. 27, 2000

Related U.S. Application Data

(60) Provisional application No. 60/194,548, filed on Apr. 5, 2000.

(51) Int. Cl.$^7$ .............................. C12M 1/34; C12Q 1/04
(52) U.S. Cl. ................... 435/288.7; 435/34; 435/287.9; 435/808; 435/6; 435/7.2
(58) Field of Search .................... 435/287.1, 288.7, 435/287.9, 808, 7.2, 7.32, 29, 34, 6; 422/82.06, 82.07, 82.08

(56) References Cited

U.S. PATENT DOCUMENTS

| | | | | |
|---|---|---|---|---|
| 3,690,832 A | * | 9/1972 | Plakas | 250/303 |
| 4,447,546 A | | 5/1984 | Hirschfeld | |
| 4,802,761 A | * | 2/1989 | Bowen et al. | 356/246 |
| 4,999,306 A | * | 3/1991 | Yafuso et al. | 250/227.14 |
| 5,061,857 A | | 10/1991 | Thompson et al. | |
| 5,091,800 A | * | 2/1992 | Offenbacher et al. | 210/500.25 |
| 5,219,527 A | * | 6/1993 | Hui et al. | 385/13 |
| 5,244,813 A | | 9/1993 | Walt et al. | |
| 5,496,700 A | * | 3/1996 | Ligler et al. | 435/4 |
| 5,545,535 A | * | 8/1996 | Roth et al. | 435/29 |
| 5,766,868 A | | 6/1998 | Seto | |
| 5,809,185 A | * | 9/1998 | Mitchell | 250/227.11 |
| 5,942,189 A | * | 8/1999 | Wolfbeis et al. | 422/58 |
| 5,994,067 A | * | 11/1999 | Wood et al. | 435/6 |

* cited by examiner

*Primary Examiner*—William H. Beisner
(74) *Attorney, Agent, or Firm*—Browdy and Neimark, P.L.L.C.

(57) ABSTRACT

Sensors for detecting microorganisms in gases, liquids, and aerosols are provided which include molecular receptors to interact with the microorganisms, polymeric membranes containing luminescent reagents, optional non-drying membrane additives, an optical substrate as a sensor support, an optional conformable optical substrate or rotating film to refresh the sensor chemistry, and means for detecting the signal from the sensor. Optical sign can be enhanced by immobilizing biocidal compounds in the sensing membrane, immobilizing metal colloids in the sensing membrane, or immobilizing sol-gel coated colloidal particles in the sensing membrane.

17 Claims, 6 Drawing Sheets

Figure 2. Optical Sensor - Coupon Configuration
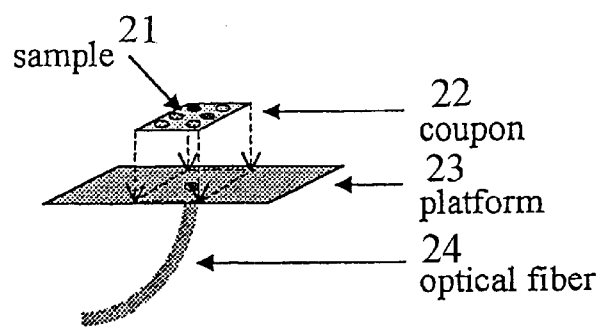
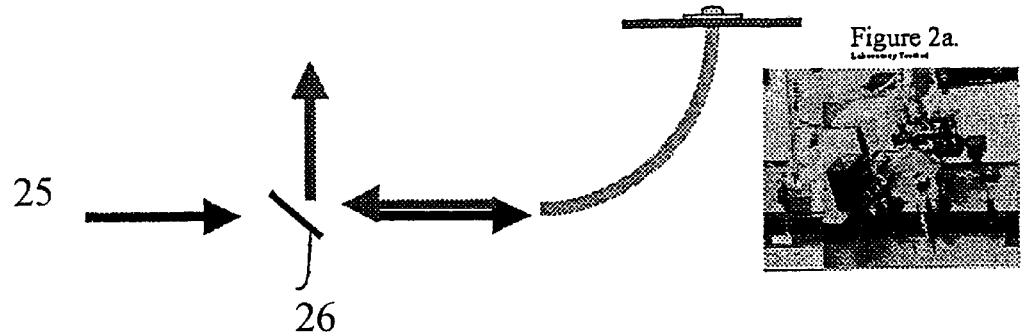
Figure 2a.

Sensor responses to Pa aerosol: intensity-time plot

[Graph showing integrated fluorescence signal vs time (hr.), with values rising from ~0 at time 0 to ~130000 at time 2 hr.]

Aerosolization of Pseudomonas (PA) suspension is achieved by using a BGI Collision Nebulizer, operated at 10 psi. The PA suspension concentration is 5 X 10e7 cells/ml. The fiber optic PA sensor uses 485 nm excitation with Syto 13 sensing chemistry. The fluorescence signal is integrated from 510 to 580 nm.

FIGURE 3

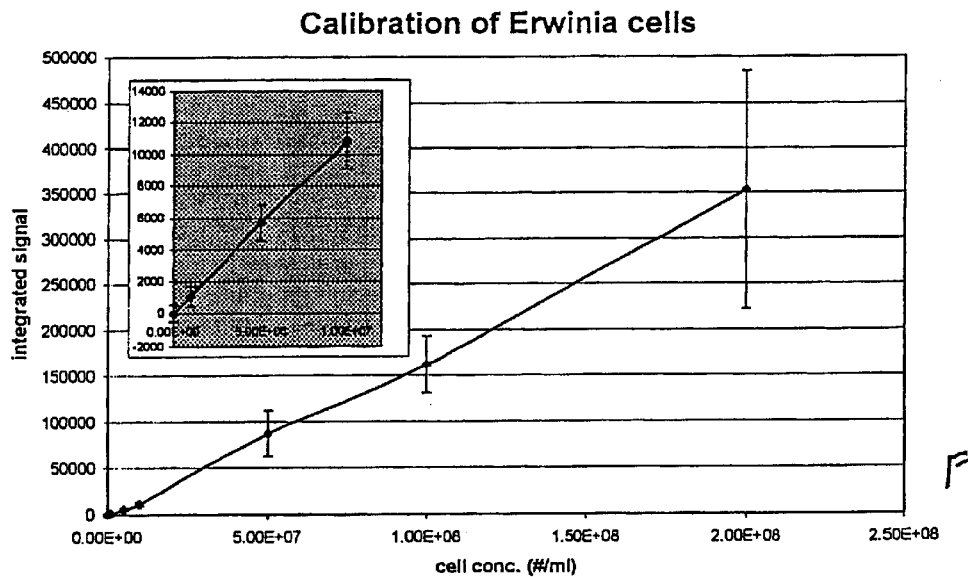

FIGURE 4

Time-based acquisition. The cell sample was freshly prepared and frozen overnight. 485 nm and 525 nm were used for excitation and fluorescence collection, respectively. The PMT integration time was set as 2s. The error bars represent one standard deviation from 3 measurements. Data are taken from 20 min sensor responses. The inset in the calibration curve details the sensor responses in low cell concentration range. LOD of EA is calculated to be 1.3e6/ml.

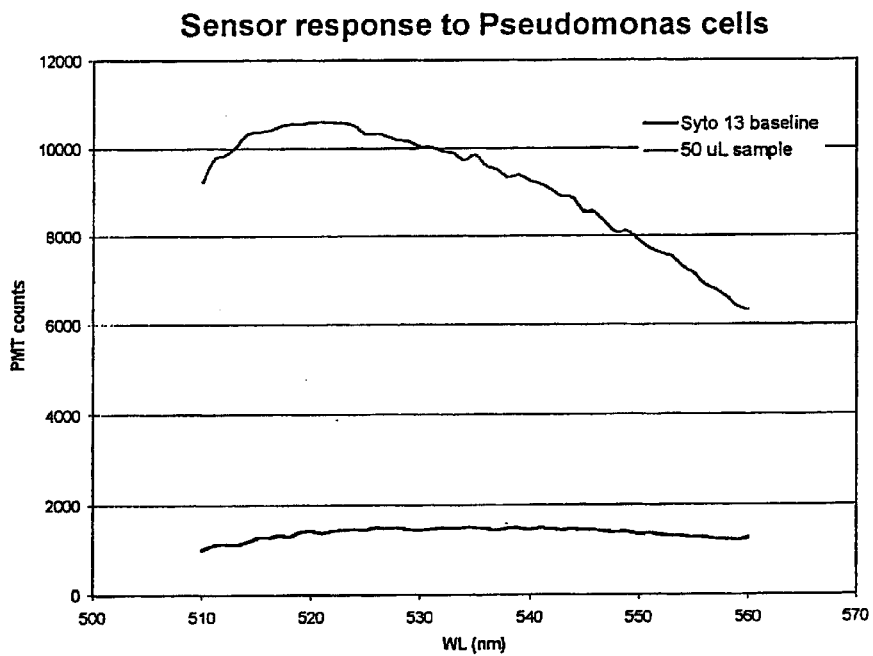

FIGURE 5

The test sample contains 2.4 X10e7 Pa/ml. PMT integration time is 600 ms.

METHODS FOR SIGNAL ENHANCEMENT IN OPTICAL MICROORGANISM SENSORS

CROSS-REFERENCE TO RELATED APPLICATIONS

This application claims priority from Ser. No. 60/194,548, filed Apr. 5, 2000, the entire contents of which are incorporated herein by reference.

FIELD OF THE INVENTION

The present invention relates to optical sensors which rapidly detect bacteria and other microorganisms, as well as to methods for enhancing signals in optical bacterial sensors. The sensors detect and discriminate classes of mircroorganisms using semi-selective interactions of luminescent compounds and molecular receptors with the microorganisms.

BACKGROUND OF THE INVENTION

In many cases there is a need for very rapid detection of biological substances, such as bacteria, viruses, rickettsia, fungi, other microorganisms, and their fragments. This is important for medical diagnosis as well as for agriculture, food processing, bioprocessing, water purification, and detection of biological weapons to prevent harm to a civilian population. Current detection methods include cell culture, microscopy, immunoassay, nucleic acid probes, and optical detectors. Assay times vary from minutes to days. Only culture and polymerase chain reaction (PCR) based tests are very sensitive. Culture and microscopy depend on isolating the intact microorganisms from the milieu to be tested. For culture, the cells must be viable, but some microorganisms are viable but not culturable. Culturing and microscopic enumeration can take several days. Tests based on genetic methods, including PCR, require the presence of intact deoxyribonucleic acid (DNA) or ribonucleic acid (RNA), must be done in the laboratory, and the instrumentation is costly.

In immunoassay and immunofluorescence stain assays, a complex is formed between the antibody, the analyte recognized (from or on the microorganism) and a label or signal generator (i.e., an enzyme) that can be measured. The measurement may represent the formation of a complex, such as in sandwich immunoassays, or the lack of formation of complex, as in most competitive immunoassays. Binding of the label or signal generator to the analyte is via the antibody.

In a competitive assay, the label or signal generator is bound to an antigen similar to the analyte. As the analyte competes with the labeled antigen for binding to the antibody, the amount of signal changes. In this case as well, the label never directly attaches to the analyte.

Optical waveguide fibers have been demonstrated in the laboratory for detecting many different chemical parameters. Many of the sensors are based on the use of the used immunoassays. For example, Hirschfield, in U.S. Pat. No. 4,447,546, disclosed the use of optical fibers as waveguides which capture and conduct fluorescence radiation emitted by molecules near their surface. Thompson et al., in U.S. Pat. No. 5,061,857, disclose an optical waveguide binding sensor having improved sensitivity for use with fluorescence assays. In these patents, the analyte is specifically labeled such that the antibody analyte complex is formed on the optical fiber waveguide is detected from the fluorescent signal excited and guided toward a fluorimeter using the evanescent wave portion of the optical fiber.

Walt et al., in U.S. Pat. 5,244,813, describes the use of fiber optic sensors for detecting organic analytes in samples.

Sato, in U.S. Pat. No. 5,766,868, describes a hydrophobic membrane to obtain a count of viable microbes in industrial water, raw materials, intermediates, and products processed in the food and beverage, pharmaceutical cosmetic, and microelectronic industries. In this case a hydrophobic filtration membrane is used under conditions to contain and confine the individual microbes or colony forming unit on the surface of the membrane to allow individual detection of the suspected microbes. Microbes are detected as bright spots representing their existence individually (i.e., without cultivation), or as a colony forming unit formed after cultivation of bacteria after filtration.

Optical fibers and optical fiber strands have been used in combination with light energy absorbing dyes for medical, environmental, and chemical analytical determinations. The optical fiber strands used for analytic determinations typically are glass or plastic extended rods having a small cross-sectional diameter. When light energy is projected into one end of the fiber strand (the proximal end), the angles at which the various light energy rays strike the surface and are reflected are greater than the critical angle. These propagated rays are piped through the length of the fiber strand by successive internal reflections, and eventually exit from the opposite end of the strand, the distal end. Typically, bundles of these strands are used collectively as optical fibers in a variety of different applications.

Typically, light from an appropriate energy source is used to illuminate the proximal end of an optical fiber or a fiber bundle. The light propagates along the length of the optical fiber and a portion of this propagated light energy exits the distal end of the optical fiber and is absorbed by one or more light energy absorbing dyes. The light energy absorbing dye may or may not be immobilized, may or may not be directly attached to the optical fiber itself, may or may not be suspended in a fluid sample containing one or more analytes of interest to be detected, and may or may not be retainable for subsequent use in a second optical determination.

Once the dye has absorbed the light energy, some light energy of varying wavelength and intensity typically returns through the distal end of the optical fiber and is then conveyed through either the same fiber or a collection of fibers to a detection system where the emerging light energy is observed and measured. The interactions between the incoming light energy conveyed by the optical fiber and the properties of the light absorbing dye, both in the presence of a fluid sample containing one or more analytes of interest and in the absence of any analytes whatsoever, provide an optical basis for both qualitative and quantitative spectral determinations.

Because of the photonic, optoelectric and microcircuitry and enhanced video technology now available, a variety of light image processing and analytical systems exist which can be used to enhance, analyze, and mathematically process the light energies introduced to and emerging from the absorbing dyes in these optical analytical techniques. Typically, these systems provide components for image capture, data acquisition, data processing and analysis, and visual presentation to the user. Commercially available systems include the QX-7 image processing and analysis system sold by Quantex, Inc. of Sunnyvale, Calif., and the IM Spectrofluorescence imaging system offered by SPEX Industries, Inc. of Edison, N.J., the miniature fluorometer offered by Ocean Optics, Inc. of Sunnyvale, Calif. Each of these systems can be combined with microscopes, cameras, and/or television monitors and computer interface for automatic processing of all light energy determinations.

Fluorescence is a physical phenomenon based upon the ability of some molecules to absorb light energy at specified wavelengths (excitation frequency) and them emit light energy of a longer wavelength and at a lower energy (emission frequency). This is referred to as fluorescence if the emission is relatively long-lived, typically on the order of $10^{11}$ to $10^7$ seconds. Substances able to fluoresce share and display a number of common characteristics: they absorb light energy at one wavelength or frequency to reach a "singlet", an excited energy state, and subsequently emit light at another light frequency, returning to a "ground" energy level. The absorption and fluorescence emission spectra are thus individual for each fluorophore, and are often graphically represented as two separate curves which are slightly overlapping.

All fluorophores demonstrate the Stokes' shift, i.e., the emitted light is always at a longer wavelength relative to the wavelength of the excitation light and at a lower energy level relative to the wavelength and energy level of the exciting light absorbed by the substance. Moreover, the same fluorescence emission spectrum is generally observed irrespective of the wavelength of the exciting light and, accordingly, the wavelength and energy of the exciting light may be varied within the limits. The light emitted by the fluorophore will always provide the same emission spectrum as emerging light. Finally, fluorescence may be measured as the quantum yield of light emitted. The fluorescence quantum yield is the ratio of the number of photons emitted in comparison to the number of photons initially absorbed by the fluorophore.

Other optical phenomena which can be used to detect microorganisms include general luminescence and chemiluminescence. Luminescence is light emitted from longer lived energy state as exemplified by luminescent lanthanides used to detect bacterial spores. [Rosen, D.L., Sharpless, C., and McGown, L.B., "Bacterial Spore Detection and Determination by Use of Terbium Dipicolinate Photoluminescence," Anal. Chem., 69, 1082–1085 (1997).]

Chemiluminescence, on the other hand, refers to compounds which upon subjection to a chemical reaction, such as exidation or reduction, emit light. The intensity of the emitted light is proportional to the concentration of the agent which acted upon the chemiluminescent compound. Chemiluminescence labels for immunoassays and nucleic acid probe assays provide a high degree of sensitivity when compared to other commonly used labels. For an overview of the subject see McCapra et al., *Journal of Bioluminescence and Chemiluminescence* 4: 51–58 (1989).

Among the conventional detection methods, such as cell culture, microscopy, immunoassay and PCR analysis, none offers all of the advantages of high sensitivity, short assay times (under approximately five minutes) and low technical complexity.

SUMMARY OF THE INVENTION

It is an object of the present invention to overcome the aforesaid deficiencies in prior art.

It is another object of the present invention to provide an optical sensor for rapid, sensitive detection of microorganisms without laboratory manipulation.

It is another object of the present invention to provide semi-selective detection and discrimination of classes of microorganisms.

It is another object of the present invention to provide methods for enhancing the signal in optical microorganism sensors.

The present invention provides a rapid, sensitive sensor for detecting microorganisms particularly air, liquid-borne, and aerosolized comprising:

Molecular receptors to interact with the microorganisms

Fluorescent or luminescent reagents and combinations thereof to report the presence of microorganisms A polymer membrane to immobilize and stabilize the reagents A non-drying membrane additive to provide a suitable environment for the chemical reaction An optical substrate as a sensor support A conformable optical substrate or rotating film to refresh the sensor chemicals Miniature optical module including sources and light detectors, filters and lenses to detect the luminescent or fluorescence signal from the sensor.

The present invention thus provides a method for improving the detection limit and response time of the optical microorganism sensors using immobilized bioactive peptides.

The present invention also provides a method for improving the detection limit (sensitivity) of the optical microorganism sensors by Surface Enhanced Fluorescence (SEF) using immobilized metal colloid particles such as silver and gold colloidal particles in the sensing membrane.

Another method for enhancing the signal according to the present invention includes optimizing surface enhanced fluorescence using sol-gel coated colloidal particles co-immobilized in the sensing membrane.

These enhancement methods can be used singly or in any combination thereof.

The sensitivity, detection limit, and response time of optical microorganism sensors are improved in those systems which use biocidal peptides co-immobilized in the sensing membrane.

Alternatively, the signal is enhanced using surface enhanced fluorescence (SEF) using co-immobilized metal colloids such as silver and gold colloidal particles in the sensing membrane.

Another method for enhancing the signal includes optimizing surface enhanced fluorescence using sol-gel coated colloidal particles co-immobilized in the sensing membrane. These enhancement methods can be used singly or in any combination thereof.

BRIEF DESCRIPTION OF THE DRAWINGS

FIG. 2 shows configuration of the optical sensor according to the present invention.

FIG. 3 shows optical sensor response to Pa aerosol in an intensity-time plot.

FIG. 4 shows calibration of Erwinia cells.

FIG. 5 shows optical sensor response to Pseudomonas cells.

DETAILED DESCRIPTION OF THE INVENTION

Figure 1:
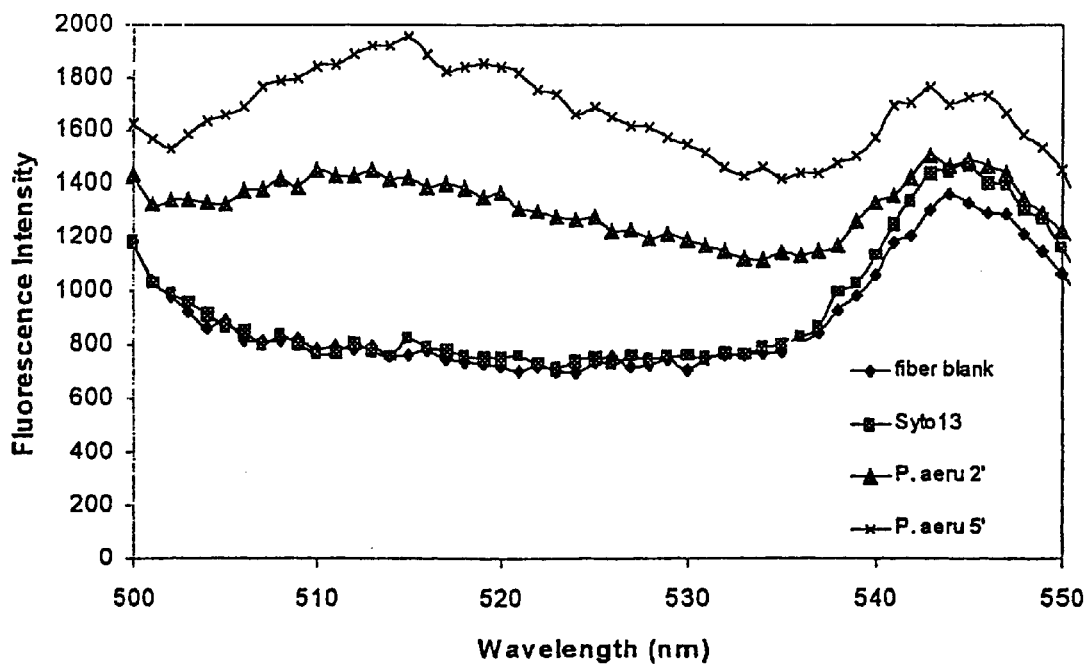
FIG. 1 shows real time sensor response to low levels of live bacteria.
Figure 6:
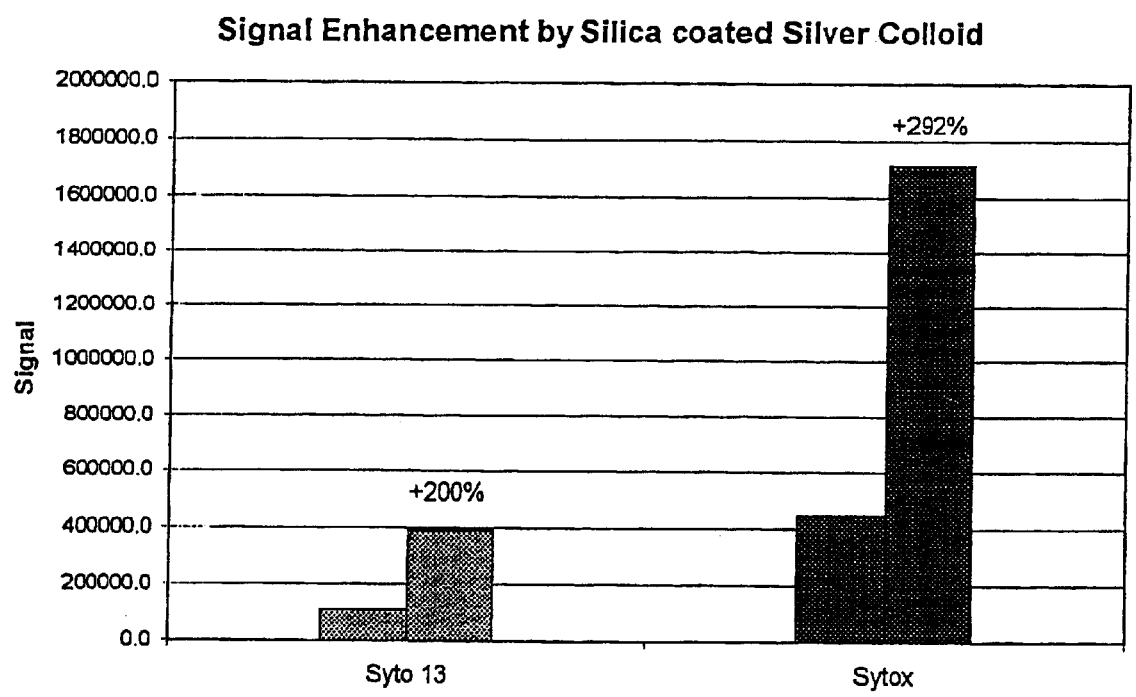
FIG. 6 shows signal enhancement by silica coated silver colloid.

To detect microorganisms according to the present invention, molecular receptors interact with microorganisms present in the sample and luminescent reagents report the presence of the microorganisms by fluorescing, luminescing, chemiluminescing, etc. The reagent are immobilized and stabilized on a polymer membrane, to which a non-drying membrane additive is added to provide a suitable environment for microorganism attachment and for the chemical reaction. An optical substrate supports the sensor materials, and a conformable optical substrate or rotating film can be provided to refresh the sensor chemicals. The signal from the sensor is detected using a miniature optical module including sources and light detectors, filters and lenses.

Among the molecular receptors that can be used are molecular recognition agents such as nucleic acid receptors such as DNA and RNA; cell wall chemicals such as peptidoglycans and diamino acids; cell membrane chemicals such as proteins, lipids, enzymes, antibodies, antigens; cellular metabolites such as ATP, NADH; and physico-chemical receptors such as pH and polarity.

A variety of luminescent reagents can be used in the present invention, depending upon the type of microorganism to be determined. Among these reagents are nucleic acid stains such as: a diverse group of cyanine type fluorescent DNA and/or RNA reactive dyes including SYTO13, SYTO17, SYTOX, SYBR Green I, SY"BR Green II; phenanthridine and acridine type DNA and RNA reactive fluorescent dyes including ethidium bromide, propidium iodide and acridine orange; indole and imicdazole type DNA and RNA reactive fluorescent dyes including DAPI and DIPI.

Other types of fluorescent probes which can be used in the present invention include anthracenes, fluoresceins, xanthenes (e.g., sulforhodamine, rhodamine), cyanine, comarin (e.g., comarin 153), oxazine (e.g. Nile blue), lanthanides such as terbium, curopium, or metal complexes or other polyaromatic hydrocarbons which produce a fluorescent signal.

Preferred fluorescent types are those which have emission wavelengths between about 300 to 888 nm.

Fluorescent pH or polarity-sensitive dyes can be used, including fluorescein, carboxyfluorescein, and their derivatives such as SNAFl (seminaphthofluoresceins), SNARF (seminaphthorhodafluoresceins) and Nile Red.

Other types of luminescent reagents are chemiluminescent reagents, such as those described in Singh et al., U.S. Pat. No. 6,002,000, the entire contents of which are hereby incorporated by reference:

These chemiluminescent reagents have the general formula:

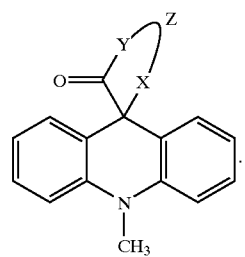

Wherein X is O or S and Y is N, Z is a chain two carbon atoms in length, said chain being part of a fused benzene ring wherein 0 to 8 hydrogens of the compound may be replaced by a W wherein each W is independently alkyl, alkylidene, aryl, aralkyl, or an alkyl, aryl, or aralkyl substituted with one or more radicals of functional groups;

wherein the functional groups are independently selected from the group consisting of carboxylic acid, alcohols, thiols, carboxamides, carbamates, carboxylic acied esters, phosphoramides, sulfonamides, ethers, sulfides, thioethers, olefins, acetylenes, amines, ketones, aldehydes, nitriles, and halogens.

The membranes used to immobilize and stabilize the reagents are membranes which are hydrophilic, adhesive to microorganisms, and chemically stable. Among the materials that can be used to immobilize and stabilize the reagents are sodium alginate, Brij52, PDDAC, polyvinyl alcohol, hydroxyethyl methacrylate, and starch.

In order to provide a suitable environment for a chemical reaction, a non-drying membrane additive such as glycerol, can be incorporated in the membrane.

A variety of optical substrates can be used in the present invention. Among these are silica optical fibers with diameters ranging from about 500 to about 1500 microns, fiber optic bundles, liquid light guides, and planar coupons or disks such as silica, fused silica, or polyvinyl chloride.

For example, an optical fiber strand can be used, which is comprised of a single optical fiber having a cylindrical shaft and two fiber ends, each of which provides a substantially planar end surface. The optical fiber is a lexible entity able to convey light energy introduced at either of its ends. These optical fibers are commercially available. The optical fiber may be cylindrical in shape or may be polygonal or asymmetrically shaped along its length. This configuration is preferable for sensing microorganisms in remote locations.

Alternatives to optical fibers are fiber optic bundles comprised of several single fibers bound together, such as liquid light guides such as sold by Oriel which have a hollow core filled with an optically transparent liquid and planar coupons such as silica, fused silica, polyvinyl chloride, and similar substances.

Planar coupons have been used extensively as optical substrates in microorganism sensors as shown in FIG. 2. These consist of a square disk of glass, quartz or plastic upon which the sensing membrane and reagents are deposited. The coupon is optically thin and transparent to visible light.

The light source for detection in the present invention can be a lamp, an LED, or a laser diode, continuous, pulsed or modulated. The detector can be a photodiode (PD), avalanche photodiode (APD), charge coupled device (CCD), or a photomultiplier tube (PMT). The response can be voltage, current, counts (as for the PMT), phase angle (as for fluorescence polarization detection), time (as for luminescence lifetime detection), or any other signal generating modality. The sensor response is directly proportional to the number of microorganism/dye complexes on the-sensing membrane, and that response can be either positive or negative (i.e., light intensity increase or attenuation).

A standard calibration curve is generated by plotting the sensor response from the detector against the number of microorganisms in an unknown test medium such as water, aerosol or solid. Alternatively, the sensor can be configured as a microorganism monitor which triggers an alarm (sound, light, vibration, etc) only when positive samples are identified.

Optical filters and lenses are used in conjunction with the detector for wavelength selection and light collection. This enables the use of different luminescent probes to detect different microorganisms, including but not limited to: bacteria, bacterial spores, fungal spores, discrimination of live versus dead bacteria, discrimination of biological from non-biological material, and viruses. The detection optics also improve the signal to noise ratio, thereby improving the detection limit of the sensor.

An optical sensor-coupon configuration is illustrated in FIG. 2. The sample 21 is placed onto the coupon 22, which in turn is placed onto platform 23 which can optionally be connected to an optical fiber or other means to carry light to a sensor 26. Fiber optics are preferred for making measurements in remote locations.

The first method for signal enhancement uses bactericidal peptides co-immobilized in the sensing membrane, e.g., Cecropin A, Cecropin B. These are small basic peptides which have bactericidal properties, and act by compromising bacterial cell membranes, rending the cellular DNA and RNA more available for reaction with the fluorescent probes. The bactericidal peptides can be immobilized in the membrane by entrapment or adsorption in the sensing membrane.

In a typical configuration the sensor chemistry is replaced after use by inserting a new sensor coupon or new optical fiber segment. Optionally, the sensor chemistry can also be occasionally refreshed using a conformal optical substrate in a rotating film configuration, operated much like the film cartridges used in cameras. This arrangement makes it possible to use the sensor over an extended period of time with the assurance that the reagents are present in sufficient amounts to provide a reliable test. These options are shown schematically in FIG. 2.

The optical module for use in the present invention is miniaturized and comprises:

A solid state light source, such as an LED, shown in FIG. 2 as 25

A solid state detector such as a photdiode, avalanche photodiode, or a channel photomultiplier tube Optical filters for wavelength selection, shown in FIG. 2 as 24

Optical lenses for light collimation, shown in FIG. 2 as 26.

Figures 7A, 7B:
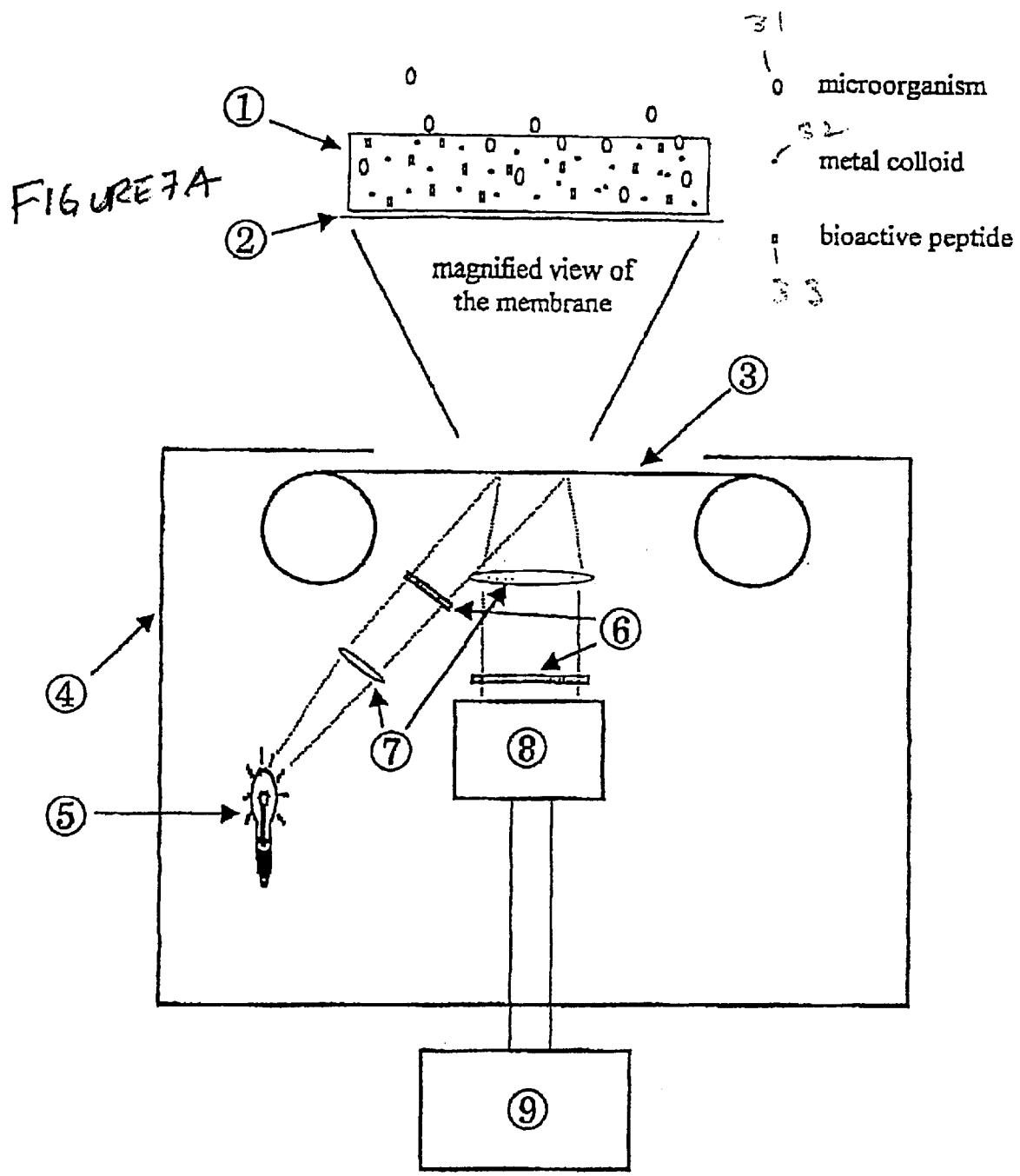
FIG. 7A shows a magnified view of the membrane.
FIG. 7B shows the configuration of the detection system according to the present invention.

FIG. 7A shows a magnified view of the polymer membrane 1 with sensing chemistry. Microorganisms 31, metal colloids 32, and bioactive peptides 33 are located within the membrane, which in turn is located on an optical substrate 2.

FIG. 7B shows the entire detection system including an optional rotating film 3 which could be substituted by a conformable, refreshable substrate (not shown) as part of a miniature optical module 4. A light source 5 directs light through lenses 7 and optical filters 6 to a photodetector 8. An amplifier, signal processing means, and readout device 9 provides readable information regarding the microorganisms on the polymer membrane.

The present invention further provides methods to enhance the signals in optical microorganism sensors. These methods enhance the sensitivity, detection limit, and response time of the optical microorganism sensors of the present invention.

Alternatively, the optical signal can be enhanced using surface enhanced fluorescence (SEF) using co-immobilized metal colloids such as silver and gold colloidal particles in the sensing membrane. Surface enhancement near the surface of metal films is due to a strong increase in the electromagnetic field in close proximity to a metal surface. This increase is due to excitation of surface plasmon resonances in the metals. Specific interactions between metal surfaces and nearby molecules also will affect the magnitude of the signal enhancement. This phenomenon has been exploited in an analytical Raman spectroscopy, in which the SEF effect is well known. The greatest effect is seen with roughened surfaces of silver or gold having nano-sized structural features. The silver and gold colloidal particles are on the order of 50-15 nm in size.

The effect is highly distance dependent, decreasing sharply with increased distance between the metal surface and the molecule. This distance can be optimized by use of a spacer layer such as a silica layer. The spacer layer is formed around the colloidal particles using standard sol-gel processing techniques, with the primary silica layer being formed from tetraethylorthosilicate (TEOS). The thickness of the silica spacer is typically 10-50 nm.

The colloids are immobilized in the polymer membrane or entrapped within the polymer membrane. The sol-gel layer spacer layer coats the metal colloid to optimize the SEF effect. The sol-gel film thickness can be tailored via processing conditions to optimize the SEF enhancement effect. The sol-gel spacer is an optically transparent layer, such as one made of glass. Surface enhancement is effected by adhering a specific partner or partners to a surface.

One method for optimizing surface enhanced fluorescence uses sol-gel coated colloidal particles co-immobilized in the sensing membrane.

The sensor of the present invention can be readily used to obtain rapid, semi-selective detection of classes detection of microorganisms. The response time can be as short as a few minutes. For example, it takes less than three minutes to test for acridine orange stain Pseudomonas cells in aqueous media for fluorescence microscope observations. Similarly, sensing films comprised SYTO13 dye can detect a fluorescent signal change in less than two minutes. Because staining of the microorganisms is less likely to occur in a relatively dry environment, glycerol or similar additive is used in the sensing membrane to stabilize the fluorescent probes and to increase the possibility for microorganism attachment. Therefor the sensors can be used to detect microorganisms in gaseous, liquid and aerosolized samples as well as on solid substrates.

The sensor detects the Stokes shift of light traveling through a fluorochrome coated waveguide in response to microorganisms fluorescing as they come into contact with the fluorochrome coating on the membrane. The sensor can be used to detect microorganisms in gases, liquids, and as well as on solid surfaces.

As microorganisms come into contact with the reagent coating on the polymer membrane, a Stokes shift occurs in the light traveling within the waveguide. Different types of fluorescent or chemiluminescent compounds are used to detect different types of microorganisms, as explained in Alice Lombardi Givan, *Flow Cytometry*, 1993, pp. 60–107, which is hereby incorporated by reference in its entity.

An optical fiber or optical fiber waveguide having a membrane containing fluorescent or chemiluminescent or other luminescent reagents presents a particular wavelength to a detector. In the presence of a microorganism which fluoresces in the presence of the reagent in the membrane, however, the wavelength of the light received at a photodetector will be shifted to another wavelength. The detector is a photocell, photomultiplier device, etc., which is tuned to detect only wavelengths of interest and then, in response, provides a signal to an indicator which can be read by an operator. Alternatively, the signal can be an audible or visible alarm.

For example, a number of particular fluorochrome compositions have been formulated, and each is usually particularly well suited to detecting certain types of microorganisms. Table I shows a number of different types of fluorochromes which may be immobilized in the polymeric membrane:

TABLE I

| Flurochrome | Chemical Name | ABS | Emis | Use |
|---|---|---|---|---|
| SYTO | | 470–520 nm | | cell permeant nucleic acid stain |
| SYTOX | | 500–523 nm | | cell permeant nucleic acid stain |
| CTC | 5-cyano-2,3-ditolyl tetrazolium chloride | 450–490 nm | 620 nm | Vital redox stain |
| DAPI | 4,6-diamino-2-phenyl indole | 365 nm | 475 nm | Nucleic acids (live cells) |
| Ethidium bromide | $C_{21}H_2ON_3Br$ | 517 nm | 625 nm | Stains DNA or dead cells |
| Acridine orange | $C_{17}H_2ON_3Cl$ | 480 nm | 510 nm | Nucleic acids (live cells) |
| FITC | fluorescein iso-thiocyanate | 480 nm | 525 nm | Detection of antigen/antibody reactions |
| Rhodamine 101 | $C_{14}H_{15}N_3Cl_2$ | Green | | Nucleic acids |
| TbCl3$_3$EuCl3 | terbium, chloride, europium chloride | 270–540 nm | | react with spore coat chemicall |
| Propidium iodide | | 493 nm | 630 nm | DNA only |

These dyes have been formulated in unique combinations for sensitive detection of many species of bacteria, bacterial spores, and viruses, and for discrimination of living from dead bacteria. These dyes have been formulated in unique combinations to discriminate bacteria and bacterial spores from chemical toxins, viruses, fungal spores, ragweed, dust, carbon black (soot), and organic vapors.

If, for example, a microorganism used as a biological. weapon, such as anthrax, is to be detected, the membrane is impregnated with a bacterial DNA\RNA stain such as SYTO13, or with TbCl$_3$ to detect the pathogenic spores arising from that bacterium, or with DAPI or acridine orange. Alternatively, if it is desired to detect non-viability of the organisms, the membrane is impregnated with ethidium bromide SYTOX. Combination of SYTO and SYTOX dye will provide broad based detection capability for bacteria no matter what their age or physiological state. Calcofluor White may be used to detect fungi to provide a rapid indication of the quality of the air within a room, building, or other space.

Experimental Section

Chemicals

Unless specified, all reagents were directly purchased from manufactures without further purification. The nucleic acid fluorescent dye STYO13, was a product of Molecular Probes, Inc. (Eugene, Oreg.). Phosphate buffered saline (PBS) and Triptic Soy Broth (TSB) were obtained from Sigma (St. Louis, Mo.) and Becton Dickinson (Sparks, Md.), respectively. Deionized distilled water was prepared from a Corning MP-6A Mega-Pure system. Pure water and PBS solutions were passed through 0.2 $\mu$m filters for sterilization and stored in the dark at 4° C.

Microorganisms

The cultivation, transfer and preparation procedures for microorganisms were performed in a Class H, Type A laminar flow biosafety cabinet (Baker Colo., Sanford, Me.) using aseptic techniques. Pa cells (strain #10145) were a product of the American Type Culture Collection (ATCC, Rockville, Md.). To prepare aqueous Pa suspension, cells were grown on Trypticase Soy Agar (TSA, Becton Dickinson, Cockeysville, Md.) plates and incubated at 30° C. for 18 to 24 hrs. Pa cells were harvested from TSA, suspended in 10 mL of 0.01M PBS buffer, and centrifuged at 5,000 rpm for 15 min. The supernatant was carefully removed and the pellet resuspended in 10 mL of PBS, followed by another centrifugation resuspension cycle. The final concentration was approximately $1\times10^9$ - cells/mL, based on an acridine orange direct count (AODC) using epifluorescence microscopy.[13]

In the Pa growth phase experiment, cells were cultured in 50 mL to TSB at 30° C. with 100 rpm of constant agitation. One milliliter of culture broth was aseptically pipetted from the bulk solution at specified time intervals (FIG. 4). One portion of this culture broth was serially diluted and transferred to TSA for viable cell count. The remaining portion of sample culture was pelleted by centrifuging at 5,000 rpm for 15 min. and washed by resuspending in 1 mL of water. One portion of the washed Pa cells were serially diluted and enumerated by the AODC method. The remaining portion of the washed Pa cells were diluted to a concentration of $3.4\times10^7$ - cells/mL, and a 1$\mu$L aliquot was used for sensor measurement.

Preparation of Sensing Films

The procedures for preparation of the sensor films were quite simple. Two microliters of a 50 $\mu$m SYTO13 aqueous solution was directly pipetted onto the distal end of a 1400 $\mu$m optical fiber. The solution was allowed to dry under ambient. conditions for 20 min. This resulted in a thin film of SYTO13 on the optical fiber's distal end.

Sensor Geometry and Preparation

A 16× microscope objective was used to focus the excitation light beam on a 800 $\mu$m (core diameter) optical fiber. The optical fiber was used to carry the excitation light to the digital end and to transport the fluorescence signal to the detector. Before assembling, serial polishing steps were applied to the distal ends of all optical fibers, and a 0.3 $\mu$m lapping film was used for the final polishing step. In FIG. 1, the sensor geometry was such that the 800 $\mu$m optical fiber end was connected to a 1400 $\mu$m optical fiber via an optical connector. The larger diameter fiber presents a greater surface area for cell capture which improves sensitivity and lifetime. However, the sensor's optical coupling efficiency was reduced somewhat because of the mismatch in core diameter between the two coupled fibers.

Sample Detection

Bacterial suspensions were either pipetted directly onto the sensor distal end or collected on the distal end during aerosolization. When samples were pipetted onto the fiber surface, sensor signals were recorded 15 minutes after application. Although the cells begin to stain immediately, 15 minutes was determined to be an optimal balance between dye reaction time and solvent evaporation. Separate experiments have shown that a signal change from a sensor exposed to ~1,000 cells can be seen in less than 2 minutes.

Aerosolized bacterial cells were introduced to a steel bioaerosol chamber having dimensions of 10×5×2.5 inches. Bacterial samples were introduced from one side of the chamber using a MRE CN-24 Collison Nebulizer (BGI Inc., Waltham, Mass.), operated at 10psi with nitrogen as the carrier gas. The carrier gas exit port and the 1400 $\mu$m fiber optic sensor were located on the opposite side of the chamber from the nebulizer opening. The sensor's distal end was positioned such that it was facing the nebulizer opening offset a distance of ~2 inches. The bacterial cell efflux from the chamber was captured using a 0.2 $\mu$m Teflon filter at the chamber exit port. As a safety precaution the aerosol chamber was leak tested before each use by submerging it in water and pressurizing it with nitrogen to 10psi.

Instrumentation

The fiber optic sensor geometry was based on the combination of proximal-face excitation and distal-end chemistry (FIG. 1). Excitation light to the sensor was provided by a 75 W Xe-arc lamp, coupled to an Acton Research Corporation (ARC, Acton, Mass.) model SpectraPro-150 monochromator. The excitation wavelength was set at 485 nm. The fluorescence signal was collected by a SpectraPro-300 monochromator with a photomultiplier tube operated at 600V. To purify the excitation beam and to eliminate stray light from the source, interference band-pass filters were used on the source monochromator exit slit and the detector monochromator entrance slit. The detector entrance slit was set at 500 $\mu$m, and the calculated resolution was 2.7 nm. Data acquisition was accomplished using a desktop computer with ARC SpectraSense data acquisition software. An ARC NCL controller box was used as the computer-spectrometer interface. The fluorescence microscope used for AODC was a Nikon Inc. (Melville, N.Y.) Eclipse E 400 system with a 100 W mercury lamp as the excitation light source.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. Thus the expressions "means to . . ." and "means for . . .", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same function can be used; and it is intended that such expressions be given their broadest interpretation.

What is claimed is:

1. A sensor for detecting microorganisms in gases, liquids, aerosols, and on surfaces, comprising:
    a. a membrane in which is immobilized at least one molecular receptor to interact with the microorganisms and at least one luminescent reagent to report the presence of microorganisms;
    b. an optical substrate as a sensor support
    c. an optical module for exciting an optical signal for detecting the fluorescence optical signal from the sensor.

2. The sensor according to claim 1 further including a conformable optical substrate or rotating film to refresh the sensor chemistry.

3. The sensor according to claim 1 wherein the molecular receptors are selected from the group consisting of molecular recognition agents, cellular metabolites, and physicochemical receptors.

4. The sensor according to claim 3 wherein the molecular receptors are selected from the group consisting of nucleic acid probes, proteins, lipid stains, redox dyes, and luminescent lanthanides.

5. The sensor according to claim 1 wherein the luminescent reagents are selected from the group consisting of fluorescent DNA, RNA-reactive dyes, luminescent lanthanides, chemiluminescent reagents, fluorescent dyes, pH-sensitive dyes, and polarity-sensitive dyes.

6. The method according to claim 1 wherein the membrane is made of materials selected from the group consisting of sodium alginate, Brij52, hydroxymethyl methacrylate, and polyvinyl alcohol.

7. The sensor according to claim 1 wherein a non-drying additive is present in the membrane.

8. The sensor according to claim 7 wherein the non-drying additive is selected from the group consisting of glycols.

9. The sensor according to claim 1 wherein the optical substrate is selected from the group consisting of silica optical fibers, fiber optic-bundles, liquid light guides, and planar coupons.

10. The sensor according to claim 1 further including a conformable optical substrate in a rotating film configuration to refresh the sensor chemistry.

11. A method for detecting microorganisms comprising:
    a. contacting a sensor comprising a membrane on which are immobilized at least one molecular receptor for microorganisms and at least one luminescent agent to report the presence of microorganisms in a sample suspected of containing at least one microorganism, said sensor being supported on an optical substrate;
    b. exciting an optical signal and detecting a fluorescence optical signal from the sensor; and
    c. using the fluorescence optical signal to determine the presence of microorganisms.

12. The method according to claim 11 wherein the membrane includes a non-drying membrane additive.

13. The method according to claim 11 wherein a conformable optical substrate or rotating film is provided with the sensor whereby the sensor chemicals are refreshed.

14. The method according to claim 11 wherein biocidal peptides are immobilized in the membrane.

15. The method according to claim 11 wherein metal colloids are immobilized in the membrane.

16. The method according to claim 15 wherein the metal colloids are selected from the group consisting of silver and gold.

17. The method according to claim 11 wherein sol-gel particles are immobilized in the membrane.

* * * * *